United States Patent [19]

Diehl et al.

[11] Patent Number: 5,292,806
[45] Date of Patent: Mar. 8, 1994

[54] COMPOSITIONS CONTAINING BLENDS OF POLYSTYRENE-POLYISOPRENE-POLYSTYRENE BLOCK COPOLYMERS

[75] Inventors: Charles F. Diehl; Jean M. Tancrede, both of Baton Rouge, La.

[73] Assignees: The Dow Chemical Company, Midland, Mich.; Exxon Chemical Patents, Inc., Linden, N.J.

[21] Appl. No.: 626,084

[22] Filed: Dec. 11, 1990

Related U.S. Application Data

[63] Continuation-in-part of Ser. No. 393,545, Aug. 11, 1989, Pat. No. 5,143,968.

[51] Int. Cl.$^5$ .............................................. C08L 53/02
[52] U.S. Cl. ............................ 525/89; 525/95; 525/98
[58] Field of Search ............... 524/387, 388, 505; 525/89, 514, 95, 98

[56] References Cited

U.S. PATENT DOCUMENTS

| | | | |
|---|---|---|---|
| 3,614,836 | 10/1971 | Snyder et al. | 36/2.5 |
| 3,635,861 | 1/1972 | Russell | 260/27 |
| 3,658,740 | 4/1972 | Marrs | 260/27 |
| 3,736,281 | 5/1973 | Russell | 260/27 R |
| 3,935,338 | 1/1976 | Robertson et al. | 427/207 |
| 4,096,203 | 6/1978 | St. Clair | 260/876 B |
| 4,163,077 | 7/1979 | Antonsen et al. | 428/355 |
| 4,205,679 | 6/1980 | Repke et al. | 128/287 |
| 4,212,910 | 7/1980 | Taylor et al. | 428/35 |
| 4,411,954 | 10/1983 | Butch, III et al. | 428/343 |
| 4,540,415 | 9/1985 | Korpman | 604/390 |
| 4,699,938 | 10/1987 | Minamizaki et al. | 525/89 |
| 4,785,043 | 11/1988 | Kawai et al. | 524/272 |
| 4,985,499 | 1/1991 | Nishikawa et al. | 525/89 |
| 4,997,709 | 3/1991 | Huddleson et al. | 428/344 |
| 5,028,646 | 7/1991 | Miller et al. | 524/271 |
| 5,089,550 | 2/1992 | Sakagami et al. | 525/314 |
| 5,149,741 | 9/1992 | Alper et al. | 525/95 |

FOREIGN PATENT DOCUMENTS

| | | |
|---|---|---|
| 0306232A2 | 3/1989 | European Pat. Off. |
| 0333936A1 | 9/1989 | European Pat. Off. |
| 0362850A2 | 4/1990 | European Pat. Off. |
| 1594267 | 8/1969 | Fed. Rep. of Germany |
| 56-090849 | 7/1981 | Japan |
| 1035873 | 6/1964 | United Kingdom |
| 1211244 | 11/1967 | United Kingdom |
| 1447419 | 4/1974 | United Kingdom |

OTHER PUBLICATIONS

Jagisch et al., "Minimal-Diblock-Content SBCs Provide Formulating Flexibility", *Adhesives Age*, Sep. 1990, pp. 24–29.

Jagisch et al., "New Styrene Block Copolymers for Tape and Label Use", Reprinted from *1990 PSTC Seminar Proceedings*, Presented at the Pressure Sensitive Tape Council Technical Seminar, Tech XIII, May 2, 1990.

Luvinh et al., "Dexco Styrenic Block Copolymers for Hot Melt Adhesives", European Industrial Adhesives Conference, Brussels, Oct. 3–5, 1990.

Meyer et al., "Tensile Strength of Joints Bonded with ABA Poly(styrene-b-isoprene) Films", *Polymer*, vol. 22, pp. 995–996, Jul., 1981.

Morton et al., "The Behaviour of Elastomers from AB; Block Polymers", SRS 4, Issue 3, Dec., 1969, pp. 70–73.

Morton et al., "Structure-Property Relationship for Styrene-Diene Thermoplastic Elastomers", *J. Polymer Sci.: Part C*, No. 26, pp. 99–115 (1969).

Widmaier et al., "Adhesives Properties of ABA Poly(styrene-b-isoprene) Block Copolymers", *Polymer*, vol. 18, Jun., 1977, pp. 587–590.

*Primary Examiner*—James J. Seidleck
*Assistant Examiner*—W. R. H. Clark
*Attorney, Agent, or Firm*—Pravel, Hewitt, Kimball & Krieger

[57] ABSTRACT

Blends of low styrene content polystyrene-polyisoprene-polystyrene block copolymer and high styrene content polystyrene-polyisoprene-polystyrene block copolymer can be used with tackifier resins, plasticizer oil and antioxidants to formulate pressure sensitive adhesives of improved cohesive strength vis-a-vis adhesives formed from the low styrene content polystyrene-polyisoprene-polystyrene block copolymer while maintaining good balance between tack, bonding characteristics and heat resistance.

11 Claims, No Drawings

COMPOSITIONS CONTAINING BLENDS OF POLYSTYRENE-POLYISOPRENE-POLYSTYRENE BLOCK COPOLYMERS

RELATED APPLICATIONS

This is a continuation-in-part of Application Ser. No. 393,545, filed Aug. 11, 1989 by Charles F. Diehl, Michael O. Myers and Jean M. Tancrede, now U.S. Pat. No. 5,143,968.

FIELD OF THE INVENTION

This invention relates to adhesive compositions constituted of blends of polystyrene-polyisoprene-polystyrene block copolymers. In particular, it relates to pressure sensitive adhesives, especially pressure sensitive hot melt adhesives, formed from blends of polystyrene-polyisoprene-polystyrene block copolymers.

BACKGROUND

Low styrene polystyrene-polyisoprene-polystyrene block copolymer, or copolymers with less than 25 weight percent styrene are known to yield useful pressure sensitive adhesives when used in combination with tackifier resins, plasticizer oil, and antioxidants. These adhesives are useful in a variety of applications such as tape and label applications which require good tack in addition to the ability to bond to a wide variety of low and high energy surfaces, e.g., paper, plastic films, and metals. It is very desirable to retain tack and low temperature flexibility, good cohesive strength and heat resistance while also minimizing adhesive melt viscosity. Generally however, these properties cannot be optimized simultaneously. Increasing tack, e.g., by known techniques such as adding increasing amounts of plasticizer oil or liquid resin tackifier, generally decreases strength and heat resistance. On the other hand, increasing strength or heat resistance by increasing polymer content, or by using end-block associating resins generally raises viscosity, or decreases tack, or both. Thus there exists a need for improving cohesive strength without adversely affecting tack, bonding characteristics, heat resistance, or increasing adhesive viscosity.

OBJECTS

It is, accordingly, a primary objective of this invention to fulfill this need and others.

In particular, it is an object to provide a blend of low styrene content polystyrene-polyisoprene-polystyrene block copolymer and high styrene content polystyrene-polyisoprene-polystyrene block copolymer which, when formulated with tackifier resins, plasticizer oil, and antioxidants provide pressure sensitive adhesives, particularly pressure sensitive hot melt adhesives of high cohesive strength.

A further object is to provide a blend of low styrene content polystyrene-polyisoprene-polystyrene, as has been conventionally used to form pressure sensitive adhesives, with high styrene content polystyrene-polyisoprene-polystyrene block copolymer to provide pressure sensitive adhesives of improved cohesive strength vis-a-vis adhesives formed from low styrene content polystyrene-polyisoprene-polystyrene, without adversely affecting tack, adhesive strength or heat resistance.

A yet further, and more specific object is to provide a blend of the low styrene and high styrene content polystyrene-polyisoprene-polystyrene block copolymers, by replacing a portion of the conventional low styrene content polymer with the high styrene content polystyrene-polyisoprene-polystyrene block copolymer, which can be formulated with hard (solid) tackifier resins, plasticizer oil or liquid tackifier resin, and antioxidants to produce pressure sensitive adhesives of improved cohesive strength vis-a-vis adhesives formed from the low styrene content polystyrene-polyisoprene-polystyrene block copolymer while maintaining good balance between tack, bonding characteristics and heat resistance.

THE INVENTION

These objects and others are achieved in accordance with the present invention which embodies, as novel compositions of matter, or articles of manufacture:

(i) a blend of polystyrene-polyisoprene-polystyrene, or ABA block copolymers wherein the A component of the blend is polystyrene and the B component is polyisoprene, A) a first, or primary ABA block copolymer having an overall average molecular weight ranging from about 90,000 to about 250,000, wherein the polyisoprene has an average molecular weight ranging from about 80,000 to about 225,000, the polystyrene block has an average weight ranging from about 8,000 to about 17,000, and the overall styrene content of the block copolymer ranges up to about 24 percent, and B) a second, or secondary ABA block copolymer having an overall average molecular weight ranging from about 60,000 to about 110,000, wherein the polyisoprene has an average molecular weight ranging from about 30,000 to about 70,000, the polystyrene block has an average molecular weight ranging from about 12,000 to about 20,000, and the overall styrene content of the block copolymer ranges from about 25 percent to about 50 percent, said first ABA block copolymer and said second ABA block copolymer being blended together in proportionate amounts, one component with respect to the other sufficient to produce, when formulated with tackifier resins, plasticizer oil and an antioxidant, a pressure sensitive adhesive of increased cohesive strength vis-a-vis a pressure sensitive adhesive formed from an equal weight of said first ABA block copolymer per se, similarly formulated, while maintaining good balance of tack, adhesive strength and heat resistance;

(ii) the pressure sensitive adhesives formed therewith;

(iii) articles of manufacture made with the pressure sensitive adhesives; and (iv) the process of blending together the primary ABA, and secondary ABA block copolymers to form said compositions, or articles of manufacture.

The first ABA and second ABA block copolymer, respectively, can be characterized by any of the formulas:

$$B\text{-}(AB)_n \qquad (1)$$

where n is 2, or greater than 2;

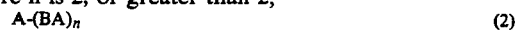

$$A\text{-}(BA)_n \qquad (2)$$

where n is 1, or greater than 1;

or $$(AB)_n \qquad (3)$$

where n is 2, or greater than 2;

wherein, in any of formulas (1), (2) or (3), A is a polystrene block and B is a polyisoprene block. The two different ABA block copolymers can thus be triblock or multi-block, and both are characterized by the presence a B block or polyisoprene block, located between two polystyrene blocks, or A blocks, which may or may not be terminal end blocks; though the A-B-A triblock copolymer is generally preferred.

The following tabulation, Table 1, identifies the general, as well as the preferred characteristics of the first ABA and second ABA block copolymers, respectively:

TABLE 1

| Component | First ABA Block Copolymer | | Second ABA Block Copolymer | |
|---|---|---|---|---|
| | General | Preferred | General | Preferred |
| Average molecular weight, A | 8000–17,000 | 10,000–14,000 | 12,000–20,000 | 13,000–19,000 |
| Average molecular weight, B | 80,000–225,000 | 90,000–140,000 | 30,000–70,000 | 40,000–70,000 |
| Overall Average molecular weight of ABA Block Copolymer | 90,000–250,000 | 110,000–170,000 | 60,000–110,000 | 70,000–100,000 |
| Amount of A Component present, per 100 parts of ABA Block Copolymer (wt. %) | 10–24 | 13–19 | 25–50 | 28–45 |

The styrene content and overall molecular weight of the first ABA block copolymer, ABA(I), and second ABA block copolymer, ABA(II), respectively, are key parameters for achieving a desired balance of properties in adhesive applications. Pressure sensitive adhesives (PSA) require rapid wet out of the surfaces to which they must adhere. Consequently, the overall adhesive mass must be soft, i.e., have high creep compliance or low modulus for good PSA performance.

ABA(I) block copolymers or block copolymers of the first, or primary, type are soft, i.e., are low modulus polymers due to the low styrene content and high molecular weight of the polyisoprene elastomeric midblock. Consequently these copolymers can be readily formulated to provide PSA systems with good tack along with adequate cohesive strength and heat resistance for most applications. However, as earlier stated, it is often desirable to improve tack; particularly at low temperatures. This can be done by increasing the plasticizer oil or liquid resin content of the adhesive mass, which further dilutes the styrene domains of the ABA(I) block copolymer; but, this leads to a loss in cohesive strength and heat resistance. In contrast, however, it was found that the use of the higher styrene content ABA(II) block copolymer in combination with the ABA(I) block copolymer, or blend of the ABA(II) and ABA(I) block copolymers, provides improved cohesive strength without adversely affecting tack properties.

The ABA(I) and ABA(II) block copolymers, when blended together, thus play different roles in a PSA system. The ABA(I), or soft ABA block copolymer, is thus largely responsible for tack development and low temperature flexibility in the PSA system. The ABA(II) block copolymer, on the other hand, provides improved cohesive strength and maintains heat resistance without adversely affecting tack properties. In order to provide these properties the composition and molecular weight of the ABA(II) block copolymer are critical factors. The high styrene content stiffens, or raises the modulus of the ABA(II) block copolymer, and therefore helps increase the cohesive strength by increasing the level of hard styrene domain structure in the adhesive system. Although the ABA(II) block copolymer would be too stiff (hard) to be used per se as a "primary", or ABA(I) copolymer, in a PSA system, its polyisoprene midblock nevertheless contributes to the flexibility and compatibility of the adhesive system.

The overall molecular weight of the secondary, or ABA(II) block copolymer, is also chosen to maintain, or lower, the overall viscosity of the adhesive system.

Low molecular weight, aromatic resins can also be used to improve the cohesive strength of adhesives systems made with low styrene, primary or ABA(I) block copolymers. These resins generally have high softening points, e.g., 120°–160° C., and are brittle solids at room temperature. They associate primarily with the styrene domains of the ABA block copolymer component and thereby stiffen the overall adhesive mass resulting in higher cohesive strength but with a subsequent loss of tack. The use of high styrene, secondary ABA(II) block copolymers, however, overcomes these problems.

Suitably, in forming the block copolymer blend (i), from about 40 parts to about 95 parts, preferably from about 60 parts to about 80 parts, of the first ABA block copolymer, ABA (I), is blended with from about 5 parts to about 60 parts, preferably from about 20 parts to about 40 parts, of the second ABA block copolymer, ABA (II). The pressure sensitive adhesive composition (ii) is formed by admixing the blend of ABA (I) and ABA (II) block copolymers with compatible primary tackifying resins, a plasticizer oil or secondary tackifying resin, or both, and an antioxidant. The compatible primary tackifying resin with which the ABA (I) and ABA (II) block copolymers are admixed may be the same or different, but generally better results are obtained by the use of different primary tackifying resins in any given formulation since ABA (I) and ABA (II) differ one from another in styrene content, this leading to differences in modulus. Thus, for best results, it is necessary to use a combination of primary tackifying resins in any given formulation; a first for ABA (I) based on the compatibility of ABA (I), and a second for ABA (II) based on the compatibility of ABA (II).

The pressure sensitive adhesive composition (ii) are preferably comprised of, per 100 parts of the blend of ABA (I) and ABA (II) block copolymers, from about 80 parts to about 225 parts, preferably from about 90 parts to about 180 parts, of the primary tackifying resins, and from about 0 parts to about 100 parts, preferably from about 0 parts to about 50 parts of the plasticizer oil or secondary tackifying resin, or admixture of both the plasticizer oil and secondary tackifying resin, based on weight. The blend will also contain from about 0.1 percent to about 2 percent, preferably from about 0.5 percent to about 1.5 percent, of an antioxidant, based on the weight of the adhesive composition.

The primary tackifying resins useful in the practice of this invention include hydrocarbon resins, synthetic polyterpenes, rosin esters and natural terpenes which are semi-solid or solid at ambient temperatures, and soften or become liquid at temperatures ranging generally from about 70° C. to about 135° C., preferably from about 85° C. to about 120° C. Exemplary of the primary tackifying resins are compatible resins such as (1) natural and modified rosins such, for example, as gum rosin, wood rosin, tall oil rosin, distilled rosin, hydrogenated rosin, dimerized rosin, and polymerized rosin; (2) glycerol and pentaerythritol esters of natural and modified rosins, such, for example, as the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; (3) copolymers and terpolymers of natured terpenes, e.g., styrene/terpene and alpha methyl styrene/terpene; (4) polyterpene resins having a softening point, as determined by ASTM method E28-58T, of from about 80° to 150° C.; the latter polyterpene resins generally resulting from the polymerization of terpene hydrocarbons, such as the bicylic monoterpene known as pinene, in the presence of Friedel-Crafts catalysts at moderately low temperatures; also included are the hydrogenated polyterpene resins; (5) phenolic modified terpene resins and hydrogenated derivatives thereof such, for example, as the resin product resulting from the condensation, in an acidic medium, of a bicyclic terpene and a phenol; (6) aliphatic petroleum hydrocarbon resins having a Ball and Ring softening point of from about 70° to 135° C.; the latter resins resulting from the polymerization of monomers consisting primarily of olefins and diolefins; also included are the hydrogenated aliphatic petroleum hydrocarbon resins; (7) aromatic petroleum hydrocarbon resins, and mixed aromatic and aliphatic paraffin hydrocarbon resins, and the hydrogenated derivatives thereof; (8) aromatic modified alicyclic petroleum hydrocarbon resins and the hydrogenated derivatives thereof; and (9) alicyclic petroleum hydrocarbon resins and the hydrogenated derivatives thereof.

The preferred primary tackifier is dependent on the amount and relative amounts of the ABA (I) and ABA (II) employed in the blend. The selection of a particular primary tackifier is thus dependent upon the specific copolymer employed, and the amount of the specific copolymer employed. The preferred tackifiers for the ABA (I) block copolymer are represented by those species described by reference to sub-paragraphs (2), (3), (4) and (6) supra. The preferred tackifiers for the ABA (II) block copolymer are represented by those species described by reference to sub-paragraphs (2), (3), (5), (7) and (8), supra.

Suitable secondary tackifying resins are those named species wherein the resin is a liquid at ambient temperature.

Various plasticizing oils are useful in the practice of this invention. The plasticizing oil can be used in place of or in combination with the secondary tackifier to reduce viscosity and improve tack properties. Plasticizing oils which have been found useful include olefin oligomers and low molecular weight polymers as well as vegetable and animal oils and their derivatives. The petroleum derived oils which may be employed are relatively high boiling materials containing only a minor proportion of aromatic hydrocarbons (preferably less than 30% and, more particularly, less than 15% by weight of the oil). Alternately, the oil may be totally non-aromatic. The oligomers may be polypropylenes, polybutenes, hdyrogenated polyisoprene, hydrogenated polybutadiene, polypiperylene and copolymers of piperylene and isoprene, or the like having average molecular weights between about 350 and about 10,000. Vegetable and animal oils include glyceryl esters of the usual fatty acids and polymerization products thereof.

The stabilizer, or antioxidant, used in accordance with the practice of this invention includes high molecular weight hindered phenols and multifunctional phenols such as sulfur and phosphorous-containing phenols. Hindered phenols are well known to those skilled in the art and may be characterized as phenolic compounds which also contain sterically bulky radicals in close proximity to the phenolic hydroxyl group thereof. In particular, tertiary butyl groups generally are substituted onto the benzene ring in at least one of the ortho positions relative to the phenolic hydroxy group. The presence of these sterically bulky substituted radicals in the vicinity of the hydroxyl group serves to retard its stretching frequency and, correspondingly, its reactivity; this steric hindrance thus providing the phenolic compound with its stabilizing properties. Representative hindered phenols include: 1,3,5-trimethyl 2,4,6-tris (3,5-di-tert-butyl-4-hydroxybenzyl) benzene; pentaerythrityl tetrakis-3(3,5-di-tert-butyl-4-hydroxyphenyl) propionate; n-octadecyl-3 3,5-di-tert-butyl-4-hydroxyphenyl)propionate; 4,4'-methylenbis (2,6-tert-butylphenol); 4,4'-thiobis (6-tert-butyl-o-cresol); 2,6-di-tert-butylphenol; 6-(4-hydroxyphenoxy)-2,4-bis(n-octyl-thio)-1,3,5 triazine; di-n-octadecyl 3,5-di-tert-butyl-4-hydroxybenzylphosphonate; 2-(n-octylthio) ethyl 3,5-di-tert-butyl-4-hydroxy-benzoate; and sorbitol [hex 3-(3,5-di-tert-butyl-4-hydroxyphenyl)-propionate.]

The pressure sensitive adhesive composition can be formed by admixture of the required components in molten state, or the components can be dissolved in a suitable hydrocarbon solvent, e.g., an aromatic hydrocarbon such as benzene, toluene, xylene or the like, or an aliphatic hydrocarbon such as hexane, heptane or the like. For example, the adhesive composition can be prepared by melt mixing the ABA (I) and ABA (II) block polymers with the primary tackifying resin(s), the secondary tackifying resin and/or plasticizing oil and stabilizer, in any order or sequence, or these materials can be added together simultaneously to form the adhesive composition. In commercial practice it would be expected that the primary tackifying resin(s) and the blend of ABA copolymers, with or without the simultaneous addition of the secondary tackifying resin or plasticizing oil, and stabilizer, would be blended together at sufficiently elevated temperature to form a fluid melt. For example, the ABA block copolymers can be blended with the solid compatible primary tackifying resin(s) and stabilizer at temperatures ranging from about 130° C. to about 200° C., preferably at from about 150° C. to about 180° C., to form a fluid melt. The secondary liquid tackifying resin or plasticizing oil can then be added to the melt.

The pressure sensitive adhesives of this invention can be mixed and coated as a hot melt mass, dissolved in and applied from hydrocarbon solvents, and applied to a backing substrate, e.g., paper, cloth, film, metal foil, tape or the like, by coating techniques conventionally used for this purpose in the adhesive tape industry. The adhesive may be coated on one or both sides of the substrate depending upon its intended use. These adhesives are particularly useful in tape and label applications, packaging, bookbinding and disposable applications. The adhesive compositions are particularly useful; e.g., in the construction of a disposable article comprised of polyethylene or polypropylene bonded to a tissue, non woven, polyethylene or polypropylene substrate; or in packaging application to bond a wide variety of high and low energy surfaces, i.e., paper, plastic, films, metals or the like.

The following non-limiting examples and comparative data, bring out the more salient features of the invention. All parts are given in parts per hundred parts of ABA block copolymers except as may otherwise be indicated.

In conducting the following tests the composition and properties of the neat A-B-A block copolymers which were prepared for making the adhesive compositions were determined by techniques "a", "b", and "c". In evaluating the performance characteristics of the adhesive compositions produced from the A-B-A block copolymers test procedures "d" through "h" were employed, to wit:

a. Styrene content of the experimental A-B-A block copolymers was determined from the proton nmr spectra. Samples were dissolved in a mixture of deuterated tetrachloroethane and tetrachloroethylene, and analyzed on a Burker 90 MHz spectrometer. Styrene content was calculated from the spectra by the method of V. D. Mochel, *Rubber Chem. and Tech.*, 40, 1200 (1967).

b. Molecular Weight of the A-B-A block copolymers was determined by GPC, using the method described by J. R. Runyon, et al, *J. Polym. Sci.* 13, 2359 (1969).

c. Melt Flow Rate (MFR) of the A-B-A copolymers was determined according to ASTM method D-1238-82, using condition "G" (200 C, 5 Kg weight).

d. Adhesive Melt Viscosity (ASTM D-3236)—Melt viscosities were measured at a temperature of 177° C., using a Brookfield Thermosel viscometer.

e. Shear Adhesion Failure Temperature (SAFT) is a measure of the ability of the bond to withstand an elevated temperature rising at 10° F./15 min., under a constant force which pulls the bond in the shear mode. Bonds 1 inch by 1 inch were formed of adhesive, on a Mylar (polyester) backing, to a stainless steel panel, using a 4.5 lb. rubber roller. The panel was suspended vertically in an oven at 30° C., and allowed to come to equilibrium. A 1 kg weight was suspended from the free end of the adhesive tape, and the temperature was raised at 10° F./14 min. The temperature at which the tape and weight fell from the panel was recorded. SAFT was reported as the average of five such determinations.

f. Shear Holding Power (Static Time to Failure Bond Test)—The cohesive strength at room temperature of the adhesives was determined according to the general procedures outlined in PSTC-7 and ASTM C-3654. A 0.5 inch by 0.5 inch bond was applied to a stainless steel panel with a 4.5 lb rubber roller. The plate was suspended vertically and a 2 kg weight was suspended from the free end of the tape. The time at which the tape and weight fell from the panel was recorded. The shear hold (in hours) was reported as the average of five such determinations. Long failure times are desirable, since they indicate strong bonds.

g. 180 Degree Peel Adhesion of the adhesives was determined according to the procedures outlined in PSTC-1 of the Pressure Sensitive Tape council. A 1 inch by 6 inch strip of the adhesive tape (2 mil Mylar backing) was applied to a stainless steel panel with a 4.5 lb. rubber roller. The tape was then peeled back over itself at 180 degree in a tensile tester at a constant crosshead speed of 12 in/min. The average force required to peel the tape from the panel was recorded. The 180 peel (lb/in) was reported as the average of five such determinations.

h. Quick Stick is that property of a pressure adhesive, which causes it to adhere to a surface instantly using no external pressure to secure a thorough bond. Quick stick is measured as the force resisting peeling of a tape at 90 degrees from a standard surface upon which it has been applied under no other pressure than the weight of the tape itself. Quick stick was measured using a tensometer with a crosshead speed of 12 in/min. The quick stick was reported as the average of five determinations according to PSTC-5.

EXAMPLES 1-13

Three ABA block copolymers, the first a low styrene content ABA block copolymer (18% styrene; 122,000 overall molecular weight) of melt flow rate (11 dg/min MFR) known useful in the formulation of pressure sensitive adhesives, e.g., PSA tapes and labels, hereinafter "DPX-511," and the two others high styrene content ABA block copolymers of the type disclosed and claimed in U.S. Pat. No. 5,143,968, supra, were employed to conduct a series of tests tabulated, for convenience, below. The first formulation, designated "0" and employed as a control in Tables 3 and 4, utilized 100% of the ABA block copolymer "DPX-511" to form a pressure sensitive adhesive with a compatible primary tackifying resin ESCOREZ 1310LC, TUF-FLO 6056 plasticizer and INORGANOX 1010 stabilizer. The high styrene content, ABA block copolymer designated "DPX-505," employed in formulation 1-6, or Examples 1-6, had an overall molecular weight of 77,000 a styrene content of 44%, and a melt flow rate of 40 dg/min. The high styrene content ABA block copolymer employed in Examples 7-13, designated DPX-506, had an overall molecular weight of 93,000, a styrene content of 29%, and a melt flow rate of 15 dg/min. Table 2 further summarizes and identifies other properties of the three ABA block copolymers. Amount of A Component Present Per 100 Parts of ABA

TABLE 2

| | Amount of A Component Present Per 100 Parts of ABA | | | |
|---|---|---|---|---|
| ABA Block Copolymer | Average Molecular Weight of A | Average Molecular Weight of B | Overall Average Molecular Weight of ABA | Amount of a Component Present per 100 Parts of ABA |
| DPX-511 | 10,980 | 100,040 | 122,000 | 18 |

TABLE 2-continued

Amount of A Component Present Per 100 Parts of ABA

| ABA Block Copolymer | Average Molecular Weight of A | Average Molecular Weight of B | Overall Average Molecular Weight of ABA | Amount of a Component Present per 100 Parts of ABA |
|---|---|---|---|---|
| DPX-505 | 16,940 | 43,120 | 77,000 | 44 |
| DPX-506 | 13,485 | 66,030 | 93,000 | 29 | the entire amount of the DPX-511 was replaced by the DPX-505. In Examples 7–10 increasing portions of the DPX-511 was replaced by DPX-506, and in Example 11 DPX-506 was substituted for DPX-511. In the control, and in all of Examples 1–11 the total formulations contained 100 parts of ABA block copolymer. In Examples 12–13, 20 parts of PICCOTEX 120 and KRISTALEX 5140, respectively, was substituted for the DPX-511.

In each of the fourteen pressure sensitive adhesive formulations, performance characteristics were made via test procedures "d" through "h", supra, and the results of each are given in Tables 3 and 4.

TABLE 3

|  | -0- | -1- | -2- | -3- | -4- | -5- | -6- |
|---|---|---|---|---|---|---|---|
| DPX-511[1] | 100 | 80 | 80 | 60 | 40 | | |
| DPX-505[1] | | 20 | 20 | 40 | 60 | 100 | 100 |
| ESCOREZ 1310LC[2] | 125 | 125 | 100 | 75 | 50 | | 125 |
| ECR-165A[2] | | | 25 | 50 | 75 | 125 | |
| TUFFLO 6056[3] | 15 | 15 | 15 | 15 | 15 | 15 | 15 |
| IRGANOX 1010[4] | 2.4 | 2.4 | 2.4 | 2.4 | 2.4 | 2.4 | 2.4 |
| Melt Viscosity, cps 177° C. | 143,000 | 262,000 | 96,750 | 51,000 | 32,400 | 12,500 | >300,000 |
| Rolling Ball, cm | 8.7 | 10 | 8.7 | 15 | 30+ | 30+ | 30+ |
| Polyken Tack, gm | 1480 | 1540 | 1610 | 1600 | 700 | 0 | 370 |
| SAFT, °C. | 94 | 93 | 94 | 94 | 94 | 91 | 95 |
| Hold to SS, Hrs (0.5 × 0.5, 2 kg) | 20 | 84 | >100 | >100 | >100 | >100 | >100 |
| Peel to SS, lb/in | 4.7 | 5.0 | 4.6 | 4.4 | 4.5 | 0.9 | 4.2 |
| Quick Stick, lb/in | 3.3 | 3.3 | 3.6 | 3.3 | 3.4 | 0 | 2.8 |

[1] Experimental ABA polymers.
[2] "ESCOREZ" is a trademark of Exxon Chemical Company. ECR-165 is an experimental $C_5/C_9$ tackifier manufactured by Exxon Chemical Company.
[3] "TUFFLO" is a trademark of Lyondell Petroleum Company.
[4] "IRGANOX" is a trademark of Ciba-Geigy.

TABLE 4

|  | -0- | -7- | -8- | -9- | -10- | -11- | -12- | -13- |
|---|---|---|---|---|---|---|---|---|
| DPX-511 | 100 | 80 | 80 | 60 | 40 | | 80 | 80 |
| DPX-506 | | 20 | 20 | 40 | 60 | 100 | | |
| ESCOREZ 1310LC | 125 | 125 | 100 | 75 | 50 | | 125 | 125 |
| ECR-165A | | | 25 | 50 | 75 | 125 | | |
| PICCOTEX 120[5] | | | | | | | 20 | |
| KRISTALEX 5140[5] | | | | | | | | 20 |
| TUFFLO 6056 | 15 | 15 | 15 | 15 | 15 | 15 | 15 | 15 |
| IRGANOX 1010 | 2.4 | 2.4 | 2.4 | 2.4 | 2.4 | 2.4 | 2.4 | 2.4 |
| Melt Viscosity, cps 177° C. | 143,000 | 266,500 | 68,000 | 37,600 | 30,800 | 21,200 | 58,000 | 140,000 |
| Rolling Ball, cm | 8.7 | 7.3 | 5.2 | 8.9 | 13.6 | 30+ | 30+ | 30+ |
| Polyken Tack, gm | 1480 | 1850 | 1690 | 1700 | 536 | 130 | 600 | 510 |
| SAFT, °C. | 94 | 94 | 97 | 95 | 93 | 87 | 91 | 97 |
| Hold to SS, Hrs (0.5 × 0.5, 2 kg) | 20 | 50 | >100 | >100 | >100 | >100 | >100 | >100 |
| Peel to SS, lb/in | 4.7 | 6.0 | 5.9 | 5.3 | 4.4 | 3.9z | 5.7 | 5.4 |
| Quick Stick, lb/in | 3.3 | 3.9 | 4.0 | 3.3 | 3.1 | 1.9z | 3.5z | 3.8z |

[5] "PICCOTEX" and "KRISTALEX" are trademarks of Hercules, Inc.

In using either DPX-505 or DPX-506 to formulate the pressure sensitive adhesive, a better balance of adhesive properties was achieved when a blend of primary tackifying resins was used. In Examples 2–4 and 8–10 the amount of ECR-165A (an aromatic/aliphatic hydrocarbon resin with 105° C. softening point) and ESCOREZ 1310 LC (an aliphatic hydrocarbon resin with 93° C. softening point) was generally used in proportionate amounts relative to the amount of high and low styrene content ABA polymers, respectively.

The TUFFLO 6056 plasticizer and IRGANOX 1010 stabilizer was then added. These components, the amounts of these components, and additional components, i.e., PICCOTEX 120 and KRISTALEX 5140, and the amount of each used, are specifically designated in Tables 3 and 4.

In Examples 1–4, a portion of the DPX-511 was progressively replaced by DPX-505, and in Examples 5–6

With reference to Tables 3 and 4, the following observations can thus be made:

Examples 1–4 show the benefit of a partial replacement of the low styrene content ABA block copolymer, DPX-511, with the high styrene content ABA block copolymer, DPX-505 (44% styrene/40 dg/min MFR). Cohesive strength, or holding power, is improved while at the same time good tack and heat resistance are maintained. In addition, viscosity was lowered when greater than 20% of DPX-511 was replaced with DPX-505.

Examples 7–10 show similar benefits obtained by replacement of the DPX-511 with DPX-506 (29% styrene/15 dg/min MFR).

Examples 5 and 11 show that neither of the secondary ABA block copolymers have a good balance of tack, adhesion, and heat resistance relative to the primary ABA block copolymer. Examples 2–4 and 8–10 show a preferred choice of primary tackifier combinations depending on the type and amount of primary and secondary ABA block copolymers.

Examples 12 and 13 contain end block reinforcing resins based on polymerized pure aromatic monomers having softening points of 120° and 150° C., respectively. Although these resins do improve the cohesive strength, they adversely affect tack in terms of rolling ball and quick stick.

Adhesive compositions having good tack and high cohesive strength are useful in many pressure sensitive applications such as tapes and labels. The adhesive compositions can be coated from the melt or from solution onto various substrates such as paper or plastic films such as polyester, polypropylene, polyethylene, etc., or foam such as polyurethane, polystyrene, etc. The adhesive compositions of this invention as exemplified by Example 1 through 4 and 7 through 10 are clearly shown to be superior to an adhesive composition prepared from only primary, low styrene block copolymers.

Average molecular weight as used throughout the application to define the ABA block copolymers of this invention means average number molecular weight.

The polystyrene-polyisoprene-polystyrene, or ABA block copolymers described herein may be prepared using any of the well known anionic polymerization synthesis techniques for preparing linear styrenic block copolymers.

For example, an ABA block copolymer may be prepared using a process which involves the sequential addition of the monomers as described in U.S. Pat. No. 3,231,635. A simplified description of this process involves the following steps:
1. Contacting styrene monomer with an organic lithium compound (sec-butyllithium, n-butyllithium, tert-butyllithium, n-hexyllithium, iso-hexyllithium, phenyllithium, naphthyllithium) in the presence of an inert hydrocarbon diluent (cyclohexane, cyclopentane, benzene, ethylbenzene, xylene, and also mixtures of these with, e.g., pentane, isopentane, hexane, heptane, and octane), to form a living polystyrene polymer with the simplified structure A-Li (where A represents polystyrene).
2. Adding isoprene monomer to the living polystyrene polymer. The resulting living polymer has the simplified structure A-B-Li, where B represents polyisoprene.
3. Adding the remainder of the styrene monomer to form the living polymer A-B-A-Li. The living polymer is then terminated with an alcohol or water, or suitable proton donating species to form a linear ABA polymer.

Alternatively, an ABA block copolymer can be prepared using a linear coupling process as described in U.S. Pat. No. 3,465,065. A simplified description of this process involves the following steps:
1. Contacting styrene monomer with an organic lithium compound (sec-butyllithium, n-butyllithium, tert-butyllithium, n-hexyllithium, iso-hexyllithium, phenyllithium, naphthyllithium) in the presence of an inert hydrocarbon diluent (cyclohexane, cyclopentane, benzene, ethylbenzene, xylene, and also mixtures of these with, e.g., pentane, isopentane, hexane, heptane, and octane), to form a living polystyrene polymer with the simplified structure A-Li (where A represents polystyrene).
2. Adding isoprene monomer to the living polystyrene polymer. The resulting living polymer has the simplified structure A-B-Li, where B represents polyisoprene.
3. This living polymer is then "coupled" by reacting it with a linear coupling agent such as those described in U.S. Pat. No. 3,465,065 (e.g., dibromoethane-1,2), to produce a linear polymer with structure A-B-X-B-A, where X represents a residual of the coupling agent which forms the nucleus (branching point) of the block copolymer. Since X has no noticeable effect on the properties of the resulting block copolymer the polymer is said to have a linear ABA structure.

In an additional alternative process, an ABA block copolymer can be produced by using a difunctional initiator as described in U.S. Pat. No. 4,200,718. A simplified description of this process involves the following steps:
1. Contacting isoprene monomer with an organic soluble dilithium compound such as those described in U.S. Pat. No. 4,200,718 [e.g., 1,4-methylphenylbis (3-methyl-1-phenylpentylidene)bis(lithium)] in the presence of an inert hydrocarbon diluent and a polar modifier such as an ether, amine, or metal alkoxide or mixtures thereof, to form a living difunctional polyisoprene polymer with the simplified structure of Li-B-D-B-Li, where D represents a residual of the difunctional initiator.
2. Adding styrene monomer to the living difunctional polymer to form a living difunctional polymer, which can be represented as Li-A-B-D-B-A-Li. Since D has no noticeable effect on the properties of the resulting block copolymer, the polymer is said to have a linear Li-A-B-A-Li structure.
3. The living polymer is then terminated with an alcohol or water, or suitable proton donating species to form a linear ABA polymer.

It is apparent that various modifications and changes can be made without departing the spirit and scope of the invention.

Having described the invention, what is claimed is:
1. A composition of matter which comprises
a blend of A-B-A block copolymers, where the A component of each block copolymer of the blend is polystyrene and the B component is polyisoprene, said blend including
A) a first A-B-A block copolymer having an overall number average molecular weight ranging from about 90,000 to about 250,000, wherein the polyisoprene has a number average molecular weight ranging from about 80,000 to about 225,000, the polystyrene block has a number average molecular weight ranging from about 8,000 to about 17,000 and the overall styrene content of the block copolymer ranges from about 10 percent to about 24 percent, and
B) a second A-B-A block copolymer having an overall number average molecular weight ranging from about 60,000 to about 110,000, wherein the polyisoprene has a number average molecular weight ranging from about 30,000 to about 70,000, the polystyrene block has a number average molecular weight ranging from about 12,000 to about 20,000, and the overall styrene content of the block copolymer ranges from about 25 percent to about 50 percent, from about 40 parts to about 95 parts of the first A-B-A block copolymer, from about 5 parts to about 60 parts of the second A-B-A block copolymer, from about 80 parts to about 225 parts of compatible primary tackifying resin, or resins, per 100 parts by weight of the blend of block copolymers, and from about 0.1 percent to about 2 percent of a stabilizer, based on the weight of the total composition.

2. The composition of claim 1 wherein the first A-B-A block copolymer has an overall number average molecular weight ranging from about 110,000 to about 170,000, the polyisoprene block of said first A-B-A block copolymer has a number average molecular weight ranging from about 90,000 to about 140,000, the polystyrene block has a number average molecular weight ranging from about 10,000 to about 14,000, and the overall styrene content of said first A-B-A block copolymer ranges from about 13 percent to about 19 percent.

3. The composition of claim 1 wherein the second A-B-A block copolymer has an overall number average molecular weight ranging from about 70,000 to about 100,000, the polyisoprene block of said second A-B-A block copolymer has a number average molecular weight ranging from about 40,000 to about 70,000, the polystyrene block has a number average molecular weight ranging from about 13,000 to about 19,000, and the overall styrene content of said second A-B-A block copolymer ranges from about 28 percent to about 45 percent.

4. The composition of claim 1 wherein the first A-B-A block copolymer has an overall number average molecular weight ranging from about 110,000 to about 170,000, the polyisoprene block of said first A-B-A block copolymer has a number average molecular weight ranging from about 90,000 to about 140,000, the polystyrene block has a number average molecular weight ranging from about 10,000 to about 14,000, and the overall styrene content of said first ABA block copolymer ranges from about 13 percent to about 19 percent; and wherein the second A-B-A block copolymer has an overall number average molecular weight ranging from about 70,000 to about 100,000, the polyisoprene block of said second A-B-A block copolymer has a number average molecular weight ranging from about 40,000 to about 70,000, the polystyrene block has a number average molecular weight ranging from about 13,000 to about 19,000, and the overall styrene content of said second A-B-A block copolymer ranges from about 28 percent to about 45 percent.

5. The composition of claim 1 wherein from about 60 parts to about 80 parts of the first A-B-A block copolymer, and from about 20 parts to about 40 parts of the second A-B-A block copolymer is present in the composition.

6. The composition of claim 1 wherein the composition contains from about 90 parts to about 180 parts of compatible primary tackifying resin, or resins, per 100 parts by weight of the blend of block copolymers, and from about 0.5 percent to about 1.5 percent of a stabilizer, based on the weight of the total composition.

7. The composition of claim 1 wherein the composition further contains from 0 to about 100 parts of a plasticizing oil, per 100 parts by weight of the blend of block copolymers.

8. The composition of claim 1 wherein the composition further contains from 0 to about 100 parts of a secondary tackifying resin, per 100 parts by weight of the blend of block copolymers.

9. The composition of claim 6 wherein the composition further contains from about 0 parts to about 50 parts of a plastizing oil, per 100 parts by weight of the blend of block copolymers.

10. The composition of claim 6 wherein the composition further contains from about 0 parts to about 50 parts of a secondary tackifying resin, per 100 parts by weight of the blend of block copolymers.

11. The composition of claim 1 wherein the first and second ABA block copolymers are independently selected from the group consisting of:

(1) $B-(AB)_n$ wherein n is greater than or equal to 2;

(2) $A-(BA)_n$ wherein n is greater than or equal to 1; or (3) $(AB)_n$ wherein n is greater than or equal to 2.

* * * * *